US006851593B2

United States Patent
Weber et al.

(10) Patent No.: US 6,851,593 B2
(45) Date of Patent: Feb. 8, 2005

(54) SYSTEM AND METHOD FOR CONTROLLING THE STRAIN OF WEB MATERIAL

(75) Inventors: Paul A. Weber, Appleton, WI (US); Thomas Arthur Bett, Oshkosh, WI (US); Tanakon Ungpiyakul, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 23 days.

(21) Appl. No.: 10/328,759

(22) Filed: Dec. 23, 2002

(65) Prior Publication Data

US 2004/0118892 A1 Jun. 24, 2004

(51) Int. Cl.[7] ............................................. B65H 20/00
(52) U.S. Cl. ...................... 226/188; 226/118.1; 226/45; 226/108; 242/418.1
(58) Field of Search ....................... 226/188, 45, 118.1; 242/418.1

(56) References Cited

U.S. PATENT DOCUMENTS

| | | |
|---|---|---|
| 2,108,410 A | 2/1938 | Perry |
| 3,659,767 A | 5/1972 | Martin |
| 4,195,791 A | 4/1980 | Frazee, Jr. |
| 4,199,118 A | 4/1980 | Tetro et al. |
| 4,286,757 A | 9/1981 | Wirth |
| 4,442,985 A | 4/1984 | Kishi et al. |
| 4,915,282 A | 4/1990 | Martin et al. |
| 5,343,899 A | 9/1994 | Jacobsson et al. |
| 5,501,412 A | 3/1996 | McAleavey |
| 5,505,129 A | 4/1996 | Greb et al. |
| 5,671,895 A | 9/1997 | Cederholm et al. |
| 5,709,352 A | 1/1998 | Rogers et al. |
| 5,825,374 A | 10/1998 | Albertalli et al. |
| 6,168,108 B1 | 1/2001 | Morley |
| 6,547,707 B2 * | 4/2003 | Cote ........................... 493/13 |
| 6,652,686 B1 * | 11/2003 | Coenen et al. ................ 156/64 |

FOREIGN PATENT DOCUMENTS

| | | |
|---|---|---|
| DE | 2 256 882 | 12/1973 |
| DE | 40 29 927 A1 | 5/1991 |
| DE | 101 58 985 A1 | 7/2002 |
| GB | 2 078 208 A | 1/1982 |

OTHER PUBLICATIONS

International Search Report for PCT/US 03/20512 dated Nov. 3, 2003, 4 pgs.

* cited by examiner

Primary Examiner—Kathy Matecki
Assistant Examiner—Evan H Langdon
(74) Attorney, Agent, or Firm—Senniger Powers

(57) ABSTRACT

A system and method for controlling the strain of a web material supplied to a machine by adjusting a tension force applied to the web material. An operator defines a target web strain via an input device. A speed sensor senses the speed of the web material supplied to the machine at a first position and a second position and generates a speed signal representative of the difference. A tension sensor senses a tension force applied to the web prior to the first position and after the first position and generates a tension signal representative of the difference. A control system calculates web strain as a function of the tension signal and speed signal, and compares the calculated strain with the target web strain and generates a speed control signal as a function of the comparison. The feed device is responsive to the speed control signal for adjusting a speed differential of the web to adjust tension force applied to the web.

21 Claims, 7 Drawing Sheets

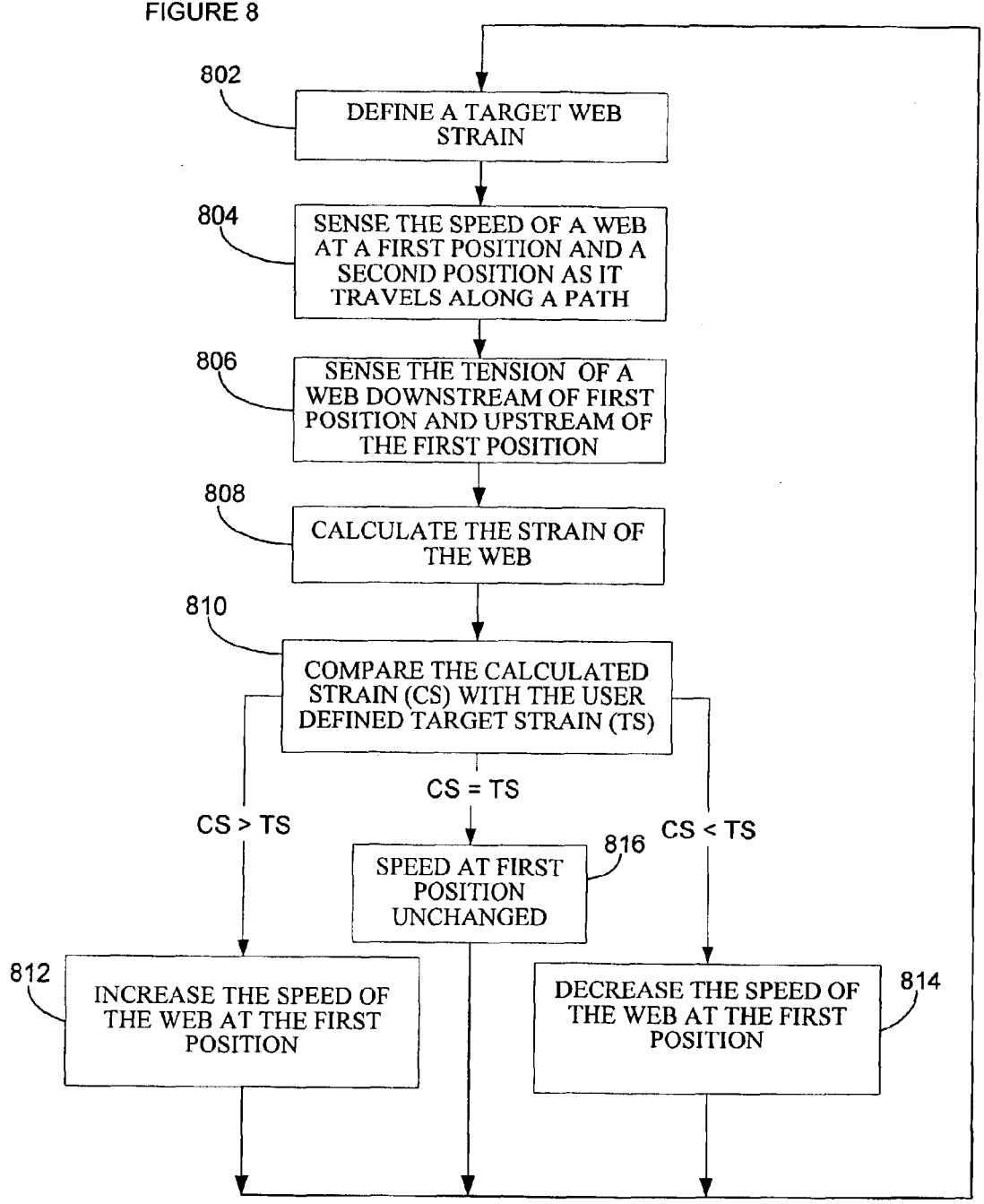

SYSTEM AND METHOD FOR CONTROLLING THE STRAIN OF WEB MATERIAL

FIELD OF THE INVENTION

The invention relates to a system and method for controlling the strain of a web by adjusting a force applied to the web. In particular, the invention relates to a system and method for maintaining the strain of a web fed to an absorbent garment manufacturing machine.

BACKGROUND OF THE INVENTION

Articles such as disposable absorbent garments have numerous applications including diapers, training pants, feminine care products, and adult incontinence products. A typical disposable absorbent garment is formed as a composite structure including an absorbent assembly disposed between a liquid permeable bodyside liner and a liquid impermeable outer cover. These components can be combined with other materials and features such as elastic materials and containment structures to form a product which is specifically suited to its intended purposes.

Absorbent garments may be formed from woven webs of material, or non-woven webs of material, or combinations thereof. In particular, a non-woven web is a web having a structure of individual fibers or threads which are interlaid, but not in a regular or identifiable manner as in a knitted or woven fabric. The term also includes individual filaments and strands, yarns or tows as well as foams and films that have been fibrillated, apertured, or otherwise treated to impart fabric-like properties. Non-woven fabrics or webs have been formed from many processes such as for example, meltblowing processes, spunbonding processes, and bonded carded web processes.

In order to avoid defects when forming diapers, and other absorbent garments from web material, it is important that the web strain be controlled during the manufacturing process. Changes in the speed of the web material within a fixed span and/or changes in the physical properties of the web material can result in elongation of a web material held at a constant tension. Defective absorbent garments can result from such elongation because it effects the relative placement product components on the web. One method of controlling web strain involves monitoring and controlling web tension during manufacturing. However, this method often proves inadequate in controlling strain variability. As a result, manufacturing tolerances can widen.

In spite of past efforts, there is a need for improved methods and systems for controlling web strain variability during a manufacturing process. There is a need for systems and methods that permit monitoring and controlling web strain during manufacturing.

The invention described below addresses one or more of these and other disadvantages and needs.

SUMMARY OF THE INVENTION

In accordance with one aspect of the invention, a system is provided for controlling a web material traveling along a path. The system includes an input device that is responsive to operator information for indicating a target strain range for the web material. A loading device applies a first tension force to the web material. A feed device applies a second tension to the web material in response to a speed control. The feed device adjusts a first speed of the web material at a first position along the path relative to a second speed of the web at a second position along the path to apply the second tension. A first force sensor senses the first tension force applied to the web material. A second force sensor senses the second tension force applied to the web material. A first speed sensor senses a first speed of the web material. A second speed sensor senses a second speed of the web material. A control system responsive to the input device, the first force sensor, the second force sensor, the first speed sensor, and the second speed sensor provides the speed control signal to the feed device to maintain the strain of the web within the target strain range as indicated by the input device.

In accordance with another aspect of the invention, a method is provided for controlling a strain of a web material. The method first includes defining a target strain range for the web material. The method further includes calculating a strain of the web material. The method further includes adjusting the tension force applied to the web material as a function of the calculated strain. The adjusting includes increasing the tension force applied to the web material when the calculated strain of the web material is less than the target strain range. The adjusting also includes decreasing the tension force applied to the web material when the calculated strain of the web material is greater than the target strain range.

Alternatively, the invention may comprise various other methods and systems. Other objects and advantages will become apparent to those skilled in the art from the detailed description herein read in conjunction with the attached drawings.

BRIEF DESCRIPTION OF DRAWINGS

FIG. 8 is an exemplary flow chart illustrating a method for managing a manufacturing processing operation according to one preferred embodiment of the invention.

Corresponding reference characters indicate corresponding parts throughout the drawings.

DETAILED DESCRIPTION

Figure 1:
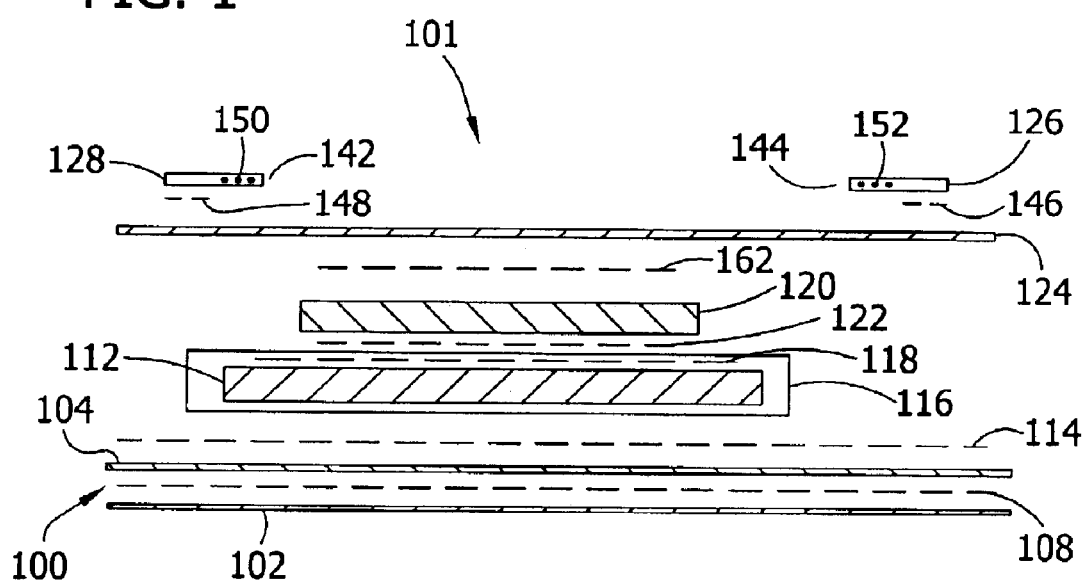
FIG. 1 is a cross sectional view of a diaper taken across line 8—8 of FIG. 3.
Figure 3:
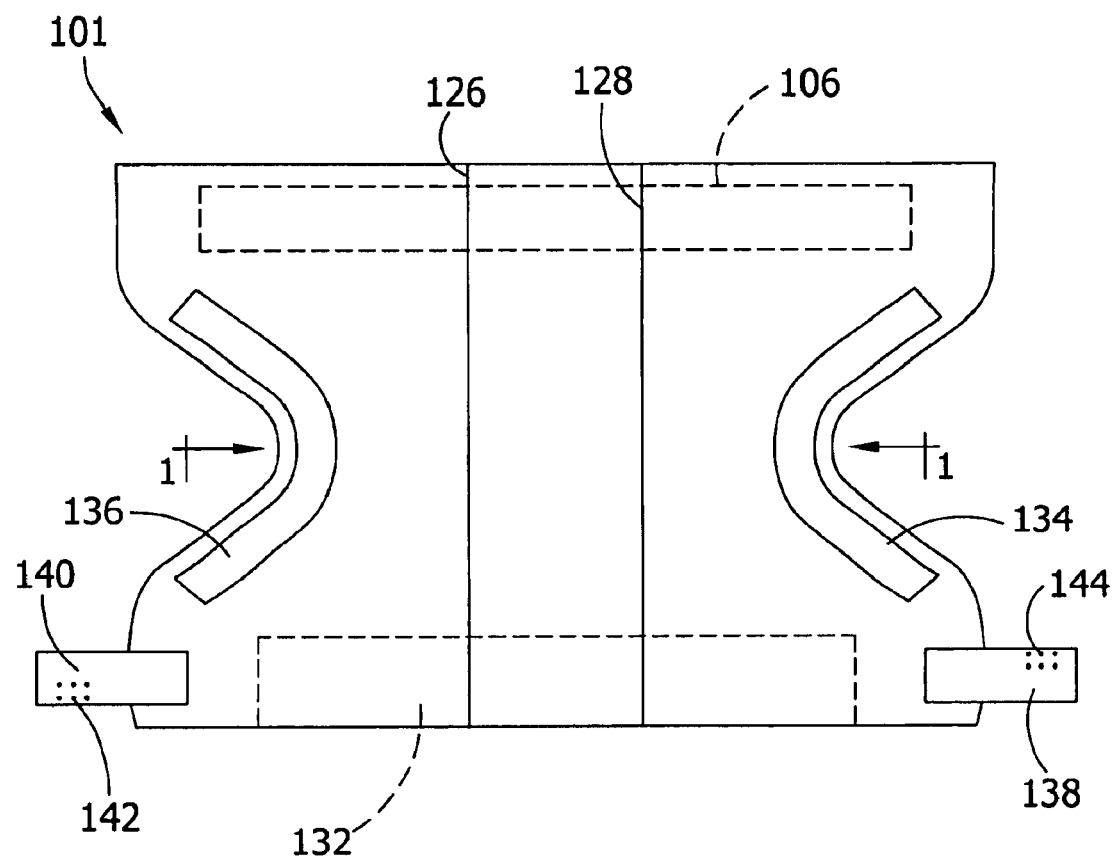
FIG. 3 is a top view of a diaper.

Referring now to FIG. 1, there is shown a cross-section of a diaper 101 along the line 8—8 of FIG. 3, which comprises generally an outer cover 100 which comprises an outer layer 102 and an inner layer 104. The outer cover 100 is desirably stretchable and may or may not be somewhat elastic. As used herein, the term "stretchable" refers to a material that may be extensible and/or elastic. That is, the material may be extended, deformed or the like, without breaking, and may or may not significantly retract after removal of an extending force. As used herein, the term "elastic" refers to that property of a material where upon removal of an elongating force, the material is capable of substantially recovering its original size and shape or the material exhibits a significant retractive force. More desirably, the outer cover 100 is extensible such that once stretched under the weight of an insulted absorbent body, the outer cover will not retract substantially back toward its original position. As used herein, the term "extensible" refers to that property of a material where upon removal of an elongating force, the material experiences a substantially permanent deformation or the material does not exhibit a significant retractive force. For example, the outer cover 100 may be stretched approximately 25% to 150% beyond its original length with a relatively low force required to extend. More desirably, the outer cover 100 may be stretched approximately 50% to 100% beyond its original length and most desirably about 50% beyond its original length under a low stretching force. As a further example, in one embodiment a 25% elongation is achieved upon application of a force of in the range of about 30 g/in to about 200 g/in, more desirably between about 70 g/in and 150 g/in and most desirably about 100 g/in. It is also contemplated that the outer cover 100 may instead be generally non-extensible and remain within the scope of this invention.

The outer cover 100 can also be desirably constructed to support a selected hydrohead of water substantially without leakage therethrough. A suitable technique for determining the resistance of a material to liquid penetration is Federal Test Method Standard FTMS 191 Method 5514, 1978, or an equivalent thereof. Since the outer cover 100 can be extensible, a layer of nylon net material having a thickness of about 0.1 mm may be needed to support the outer cover material for this test. The net material may be provided by nylon threads arranged in a hexagonal or honeycomb-like pattern with openings approximately 4 mm across. For example, the net material may be purchased from Wal-Mart Stores under the trade designation T-246. The net material is liquid pervious and does not significantly affect the hydrohead values obtained. The extensible outer cover 100 is desirably sufficiently impermeable to liquid and semi-liquid materials to substantially prevent the undesired leakage of waste materials, such as urine and feces. For example, the extensible outer cover 100 can desirably support a hydrohead of at least about 45 centimeters (cm) substantially without leakage. The extensible outer cover 100 can alternatively support a hydrohead of at least about 55 cm, and optionally, can support a hydrohead of at least about 60 cm, or more, to provide improved benefits.

The extensible outer cover 100 can be composed of various materials which provide the desired properties set forth herein. For example, the extensible outer cover 100 is desirably composed of a neckable or otherwise necked fabric, but may instead, or may additionally, be composed of a creped fabric, a crimped fiber fabric, an extendable fiber fabric, a bonded-carded fabric, a micro-pleated fabric, polymer films or the like. The fabrics may be woven or non-woven materials, such as spunbond fabrics.

As used herein, the term "neck" or "neck stretch" interchangeably means that a material is drawn such that it is extended under conditions reducing its width or its transverse dimension by drawing and elongating to increase the length of the fabric. The controlled drawing may take place under cool temperatures, room temperature or greater temperatures and is limited to an increase in overall dimension in the direction being drawn up to the elongation required to break the fabric. The necking process typically involves unwinding a sheet from a supply roll and passing it through a brake nip roll assembly driven at a given linear speed. A take-up roll or nip, operating at a linear speed higher than the brake nip roll, draws the fabric and generates the tension needed to elongate and neck the fabric. U.S. Pat. No. 4,965,122 entitled REVERSIBLY NECKED MATERIAL, by M. T. Morman which issued Oct. 23, 1990, the entire disclosure of which is hereby incorporated by reference in a manner consistent with the present document, discloses a process for providing a reversibly necked non-woven material which may include necking the material, then heating the necked material, followed by cooling.

As used herein, the term "neckable material or layer" means any material which can be necked such as a nonwoven, woven, or knitted material. The term "necked material" refers to any material which has been drawn in at least one dimension, (e.g. lengthwise), reducing the transverse dimension, (e.g. width), such that when the drawing force is removed, the material can be pulled back to its original width. The necked material typically has a higher basis weight per unit area than the un-necked material. When the necked material is pulled back to its original un-necked width, it should have about the same basis weight as the un-necked material. This differs from stretching/orienting a material layer, during which the layer is thinned and the basis weight is permanently reduced.

Typically, such necked nonwoven fabric materials are capable of being necked up to about 80 percent. For example, the extensible outer cover 100 may be composed of a material which has been necked from about 10 to about 80 percent, desirably from about 20 to about 60 percent, and more desirably from about 30 to about 50 percent for improved performance. For the purposes of the present disclosure, the term "percent necked" or "percent neckdown" refers to a ratio or percentage determined by measuring the difference between the pre-necked dimension and the necked dimension of a neckable material, and then dividing that difference by the pre-necked dimension of the neckable material and multiplying by 100 for percentage. The percent necked can be determined in accordance with the description in the above-mentioned U.S. Pat. No. 4,965,122.

The outer cover 100 is desirably a multi-layered laminate structure, and more desirably a necked, multi-layer laminate structure, to provide the desired levels of extensibility as well as liquid impermeability and vapor permeability. For example, the outer cover 100 of the illustrated embodiment is of two-layer construction, including an outer layer 102 constructed of a vapor and liquid permeable necked material and an inner layer 104 constructed of a liquid impermeable material, with the two layers being secured together by a suitable laminate adhesive 108. The outer cover may also be a single layer.

The liquid permeable outer layer 102 can be any suitable material as described above and is desirably one which provides a generally cloth-like texture. Suitable neckable materials for the outer layer 102 include non-woven webs, woven materials and knitted materials such as those described in the above-mentioned U.S. Pat. No. 4,965,122. Non-woven fabrics or webs have been formed from many processes, for example, bonded carded web processes, melt-blowing processes and spunbonding processes. The non-elastic neckable material is desirably formed from at least one member selected from fibers and filaments of inelastic polymers. Such polymers include polyesters, for example, polyethylene terephthalate, polyolefins, for example, polyethylene and polypropylene, polyamides, for example, nylon 6 and nylon 66. A preferred material for the outer layer 102 of outer cover 100 is a spunbond polypropylene. These fibers or filaments are used alone or in a mixture of two or more thereof. Suitable fibers for forming the neckable material include natural and synthetic fibers as well as bicomponent, multi-component, and shaped polymer fibers.

Many polyolefins are available for fiber production including, for example, fiber forming polypropylenes including Exxon Chemical Company's Escorene PD 3445 polypropylene and Himont Chemical Company's PF-304. Polyethylenes such as Dow Chemical's ASPUN 6811A linear low density polyethylene, 2553 LLDPE and 25355 and 12350 high density polyethylene are also suitable polymers. The nonwoven web layer may be bonded to impart a discrete bond pattern with a prescribed bond surface area. If too much bond area is present on the neckable material, it will break before it necks. If there is not enough bond area, then the neckable material will pull apart. Typically, the percent bonding area useful in the present invention ranges from around 5 percent to around 40 percent of the area of the neckable material.

One particular example of suitable material from which the outer layer 102 may be constructed is a 0.4 osy (ounce per square yard) or 14 gsm (grams per square meter) spunbond polypropylene non-woven web which is neckable in the range of about 35% to 45%. Also, while it is not a necessity for the outer layer 102 of the outer cover 100 to be liquid permeable, it is desired that it have a cloth-like texture.

The liquid impermeable inner layer 104 of the outer cover 100 can be either vapor permeable (i.e., "breathable") or vapor impermeable. The inner layer 104 is desirably manufactured from a thin plastic film, such as a thin polypropylene film, although other flexible liquid impermeable materials may also be used. More particularly, the inner layer 104 can be made from either cast or blown film equipment, can be coextruded and can be embossed if so desired. It is understood that the inner layer 104 may otherwise be made from any suitable non-elastic polymer composition and may include multiple layers. Where the inner layer 104 is vapor permeable, it may contain such fillers as micropore developing fillers, e.g. calcium carbonate; opacifying agents, e.g. titanium dioxide; and antiblock additives, e.g. diatomaceous earth. Suitable polymers for the inner layer 104 include but are not limited to non-elastic extrudable polymers such as polyolefin or a blend of polyolefins, nylon, polyester and ethylene vinyl alcohol. More particularly, useful polyolefins include polypropylene and polyethylene. Other useful polymers include those described in U.S. Pat. No. 4,777,073 to Sheth, assigned to Exxon Chemical Patents Inc., such as a copolymer of polypropylene and low density polyethylene or linear low density polyethylene.

Alternative polymers for the inner layer 104 include those referred to as single site catalyzed polymers such as "metallocene" polymers produced according to a metallocene process and which have limited elastic properties. The term "metallocene-catalyzed polymers" as used herein includes those polymer materials that are produced by the polymerization of at least ethylene using metallocenes or constrained geometry catalysts, a class of organometallic complexes, as catalysts. For example, a common metallocene is ferrocene, a complex of a metal between two cyclopentadienyl (Cp) ligands. Such metallocene polymers are available from Exxon Chemical Company of Baytown, Tex. under the trade name EXXPOL® for polypropylene based polymers and EXACT® for polyethylene based polymers and from Dow Chemical Company of Midland, Mich. under the name ENGAGE®. Desirably, the metallocene polymers are selected from copolymers of ethylene and 1-butene, copolymers of ethylene and 1-hexene, copolymers of ethylene and 1-octene and combinations thereof.

The inner layer 104 may be laminated to the neckable material of the outer layer 102 to form the laminate outer cover 100 utilizing methods known in the art including adhesive bonding, point bonding, thermal point bonding, and sonic welding. The outer cover 100 is then necked by conventional necking processes which typically vary the surface speed of the web to draw or neck the laminate. Such necking provides striated rugosities in the film and/or laminate resulting in transverse extensibility and retractability to the necked laminate and more "cloth-like" aesthetics. It is known that stretching and orienting a filled film layer (e.g., inner layer 104) causes micropores to form in the film, but longitudinal striated rugosities do not typically form in the film layer when stretched. The film layer would instead become physically thinner and may narrow slightly. By necking the laminate, the nonelastic neckable material, which is attached to the nonelastic film layer, will neck and bring the non-elastic film layer with it, thereby forming the longitudinal striated rugosities in the film which allow the film layer to extend in the transverse direction.

Alternative necked laminate materials that could be used to provide the outer cover 100 with the desired extensibility and liquid impermeability are described in U.S. patent application Ser. No. 09/460,490 filed Dec. 14, 1999 and entitled "BREATHABLE LAMINATE PERMANENTLY CONFORMABLE TO THE CONTOURS OF A WEARER", the entire disclosure of which is hereby incorporated by reference in a manner consistent with the present document. Other suitable necked laminates that include at least one non-elastic neckable material laminated to at least one non-elastic film material are described in U.S. patent application Ser. No. 09/455,513 filed Dec. 6, 1999 and entitled "TRANSVERSELY EXTENSIBLE AND RETRACTABLE NECKED LAMINATE OF NON-ELASTIC SHEET LAYERS", the entire disclosure of which is hereby incorporated by reference consistent with the present document. However, it is to be understood that the laminate outer cover need not be composed of a neckable or necked material.

Referring now to FIG. 3, diaper 101 also includes a loop material or "pub patch" 106 adhesively bound to the outer cover for receiving hook material for fastening or closing the diaper during wear. The loop material may include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may include a spunbond nonwoven web formed of single component or multi-component melt-spun filaments. For example, the pub patch may be formed from a laminated structure including a polyethylene component and a polypropylene component adhesively bonded together and the polypropylene component is outwardly facing to accept a hook-type fastener.

At least one surface of the nonwoven fabric can include a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements. Examples of suitable point-unbonded fabrics are described in U.S. Pat. No. 5,858,515 entitled PATTERN-UNBONDED NONWOVEN WEB AND PROCESS FOR MAKING THE SAME, by T. J. Stokes et al., the entire disclosure of which is incorporated herein by reference in a manner consistent with the present document.

Referring again to FIG. 1, diaper 101 additionally comprises an absorbent core 112 which can be adhesively bonded to a tissue wrap 116 (also commonly referred to as a tissue wrap sheet) by adhesive 118. Alternatively, the absorbent core need not have a tissue wrap and can simply be sandwiched between the outer cover and the bodyside liner. Absorbent core 112 may have any of a number of shapes, including rectangular, I-shaped, or T-shaped and is desirably narrower in the crotch region than in the front or back regions of the diaper 101. The size and the absorbent capacity of absorbent core 112 will be selected according to the size of the intended wearer and the liquid loading imparted by the intended use of the diaper. Further, the size and the absorbent capacity of the absorbent core 112 can be varied to accommodate various sized wearers. In addition, it has been found that the densities and/or basis weights of the absorbent core 112 can be varied. In the embodiment described herein, the absorbent core 112 typically has an absorbent capacity of at least about 300 grams of synthetic urine.

The absorbent core 112 desirably includes hydrophilic fibers and superabsorbent particles, as described more fully below. Various types of wettable, hydrophilic fibrous material can be used to form the absorbent core 112. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

The absorbent core 112 may include a combination of hydrophilic fibers and high-absorbency material. However, it is understood that absorbent bodies having absorbent layers of other compositions and having dimensions other than described may be used without departing from the scope of the present invention. More specifically, the high-absorbency material in absorbent core 112 can be selected from natural, synthetic, and modified natural polymers and materials. The high-absorbency materials can be inorganic materials, such as silica gels, or organic compounds, such as crosslinked polymers. The term "crosslinked" refers to methods for effectively rendering normally water-soluble materials substantially water insoluble but swellable. Such methods include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrrolidone), poly(vinyl morpholinone), poly(vinyl alcohol), and mixtures and copolymers thereof. Further polymers suitable for use in absorbent core 112 include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and the like. Mixtures of natural and wholly or partially synthetic absorbent polymers can also be useful in the present invention.

The high absorbency material may be in any of a wide variety of geometric forms. As a general rule, it is preferred that the high absorbency material be in the form of discrete particles or beads. However, the high absorbency material may also be in the form of fibers, flakes, rods, spheres, needles, or the like. In general, the high absorbency material is present in the absorbent core 112 in an amount of from about 5 to about 90 percent by weight, desirably in an amount of at least about 30 percent by weight, and even more desirably in an amount of at least about 50 percent by weight based on a total weight of absorbent core 112.

An example of high-absorbency material suitable for use in the absorbent core 112 is SANWET IM 3900 polymer available from Hoechst Celanese, a business having offices in Portsmouth, Va. Other suitable superabsorbents may include FAVOR SXM 880 polymer obtained from Stockhausen, a business having offices in Greensboro, N.C.

As discussed above, absorbent core 112 can be wrapped in tissue wrap 116, and adhesively bonded thereto with adhesive 118. Tissue wrap 116 is a substantially hydrophilic tissue wrap employed to help maintain the integrity of the structure of absorbent core 112 and to stabilize absorbent core 112. Tissue wrap 116 can be made of an absorbent cellulosic material, such as creped wadding or a high wet-strength tissue. Tissue wrap 116 can be configured to provide a wicking layer that helps to rapidly distribute liquid over the mass of absorbent fibers constituting the absorbent core 112.

Tissue wrap 116 can be adhesively bonded to surge management layer 120 with adhesive 122. Surge management layer 120 is typically less hydrophilic than the absorbent core 112 and has an operable level of density and basis weight to quickly collect and temporarily hold liquid surges, to transport the liquid from its initial entrance point and to substantially completely release the liquid to the absorbent core. This configuration is intended to minimize the likelihood of the liquid pooling and collecting on the portion of the diaper against the wearer's skin, thereby reducing the feeling of wetness by the wearer. The structure of the surge management layer 120 also generally enhances the air exchange within the diaper 101.

Various woven and nonwoven fabrics can be used to construct the surge management layer 120. For example, the surge management layer 120 may be a layer made of a meltblown or spunbond web of synthetic fibers, such as polyolefin fibers. The surge management layer 120 may also be a bonded-carded-web or an airlaid web composed of natural and synthetic fibers. The bonded-carded-web may, for example, be a thermally bonded web that is bonded using low melt binder fibers, powder or adhesive. The webs can optionally include a mixture of different fibers. The surge management layer 120 may be composed of a substantially hydrophobic material, and the hydrophobic material may optionally be treated with a surfactant or otherwise processed to impart a desired level of wettability and hydrophilicity. As one example, the surge management layer 120 includes a hydrophobic, nonwoven material having a basis weight of from about 30 to about 120 grams per square meter.

The absorbent core 112 is typically positioned in liquid communication with the surge management layer 120 to receive liquids released from the surge management layer, and to hold and store the liquid. In the illustrated embodiment, the surge management layer 120 is a separate layer positioned over the absorbent core 112. The surge management layer 120 serves to quickly collect and temporarily hold discharged liquids, to transport such liquids from the point of initial contact and spread the liquid to other parts of the surge management layer 120, and then to substantially completely release such liquids into the absorbent core 112.

The surge management layer 120 can be of any desired shape. Suitable shapes include for example, circular, rectangular, triangular, trapezoidal, oblong, dog-boned, hourglass-shaped, or oval.

Additional materials suitable for the surge management layer 120 are set forth in U.S. Pat. No. 5,486,166 issued Jan. 23, 1996 in the name of C. Ellis et al. and entitled "FIBROUS NONWOVEN WEB SURGE LAYER FOR PERSONAL CARE ABSORBENT ARTICLES AND THE LIKE"; U.S. Pat. No. 5,490,846 issued Feb. 13, 1996 in the name of Ellis et al. and entitled "IMPROVED SURGE MANAGEMENT FIBROUS NONWOVEN WEB FOR PERSONAL CARE ABSORBENT ARTICLES AND THE LIKE"; and U.S. Pat. No. 5,364,382 issued Nov. 15, 1994 in the name of Latimer et al. and entitled "ABSORBENT STRUCTURE HAVING IMPROVED FLUID SURGE MANAGEMENT AND PRODUCT INCORPORATING SAME", the disclosures of which are hereby incorporated by reference in a manner consistent with the present document.

The surge management layer 120 is adhesively bonded to the bodyside liner 124 with adhesive 162. The bodyside liner 124 is generally bonded to the inner layer 10 of outer cover 100 with adhesive 114 and is desirably pliable, soft feeling, and nonirritating to the wearer's skin, and is employed to help isolate the wearer's skin from the absorbent core 112. The bodyside liner 124 is less hydrophilic than the absorbent core 112, to present a relatively dry surface to the wearer, and is sufficiently porous to be liquid permeable, permitting liquid to readily penetrate through its thickness. A suitable bodyside liner 124 may be manufactured from a wide selection of web materials, but is desirably capable of stretching in at least one direction (e.g., longitudinal or lateral). Various woven and nonwoven fabrics including either or both synthetic and natural fibers can be used for the bodyside liner 124. For example, the bodyside liner 124 may be composed of a meltblown or spunbonded web of the desired fibers, and may also be a bonded-carded-web. Layers of different materials that may have different fiber deniers can also be used. The various fabrics can be composed of natural fibers, synthetic fibers or combinations thereof. For example, the bodyside liner may comprise a spunbonded polypropylene.

The bodyside liner 124 can be composed of a substantially hydrophobic material, and the hydrophobic material may optionally be treated with a surfactant or otherwise processed to impart a desired level of wettability and hydrophilicity. Examples of suitable materials for the bodyside liner 124 include 0.3–0.5 osy (10–17 gsm) polypropylene spun bond web treated with a suitable wettability treatment, 0.3–0.5 osy (10–17 gsm) bonded carded web and 0.4–0.8 osy (14–27 gsm) thru air bonded carded web. The fabric can be surface treated with an operative amount of surfactant, such as about 0.28 percent Triton X-102 surfactant. The surfactant can be applied by any conventional means, such as spraying, printing, brush coating or the like.

In particular embodiments, the bodyside liner 124 is desirably extensible and capable of extending along with the outer cover 100 for desired fit of the diaper on the wearer. For example, the bodyside liner 124 can be composed of various extensible materials such as a necked fabric, a creped fabric, a micro-pleated fabric, perforated polymer films or the like, as well as combinations thereof. The fabrics may be woven or nonwoven materials, such as spunbond fabrics, that may be elastic or non-elastic. Examples of suitable manufacturing techniques and suitable necked nonwoven fabric materials for such an extensible top sheet 61 are described in U.S. Pat. No. 4,965,122 entitled REVERSIBLY NECKED MATERIAL, by M. T. Morman which issued Oct. 23, 1990.

Desirably, the bodyside liner 124 is made from non-elastic neckable materials for reduced cost and improved manufacturing efficiency. Suitable non-elastic neckable materials for such a configuration include nonwoven webs, woven materials and knitted materials. Such webs can include one or more fabric layers. Nonwoven fabrics or webs have been formed from many processes, for example, bonded carded web processes, meltblowing processes and spunbonding processes. The non-elastic neckable material is desirably formed from at least one member selected from fibers and filaments of inelastic polymers. Such polymers include polyesters, for example, polyethylene terephthalate, polyolefins, for example, polyethylene and polypropylene, polyamides. These fibers or filaments are used alone or in a mixture of two or more thereof. Suitable fibers for forming the neckable material include natural and synthetic fibers as well as bicomponent, multi-component, and shaped polymer fibers. Many polyolefins are available for fiber production according to the present invention, for example, fiber forming polypropylenes include Exxon Chemical Company's Escorene PD 3445 polypropylene and Himont Chemical Company's PF-304. Polyethylenes such as Dow Chemical's ASPUN 6811A linear low density polyethylene, 2553 LLDPE and 25355 and 12350 high density polyethylene are also suitable polymers.

The neckable material may be necked to form the extensible bodyside liner 124 by conventional necking processes which typically vary the surface speed of the web to draw or neck the material. Such necking will allow the material to extend and retract in the transverse direction. As discussed above, such necked non-woven fabric materials typically are capable of being necked up to about 80 percent. For example, the extensible bodyside liner 124 may be necked from about 10 to about 80 percent, more desirably from about 20 to about 60 percent, and still more desirably from about 30 to about 50 percent for improved performance.

Figure 2:
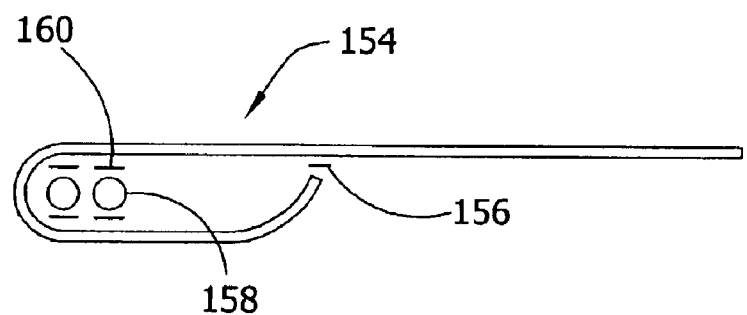
FIG. 2 is a cross sectional view of a containment flap.

Containment flaps 126 and 128 can be bonded to the outer cover, bodyside liner, or other intermediate layer. In the illustrated embodiment, the containment flaps 126 and 128 are bonded directly to the bodyside liner 124 with adhesive 146 and 148. Typically, the containment flaps are first formed outside of the diaper manufacturing process and subsequently introduced into the manufacturing process for attachment to the bodyside liner. As illustrated in FIG. 2, the containment flap 154 is formed off-line by folding the construction material for the containment flap 154 over onto itself and securing it with adhesive 156. The folding over of the material traps a stretchable material 158, secured to the containment flap 154 with adhesive 160, within the containment flap.

Referring again to FIG. 1, containment flaps 126 and 128 are configured to provide a barrier to the lateral flow of body exudates, and generally include a spunbond polypropylene and LYCRA or other stretchable material. Each containment flap typically has a free, or unattached end 142 and 144 free from connection with the bodyside liner 124 and other components of the diaper 101. Elastic strands 150 and 152 disposed within the containment flaps 126 and 128 adjacent the unattached ends thereof urge the flaps toward an upright, perpendicular configuration in at least the crotch region of the diaper 101 to form a seal against the wearer's body when the diaper is worn. The containment flaps 126 and 128 may extend longitudinally the entire length of the absorbent core 112 or they may extend only partially along the length of the absorbent core 112. When the containment flaps 126 and 128 are shorter in length than the absorbent core 112, the flaps can be selectively positioned anywhere between the side edges of the diaper and the crotch region of the diaper. In a particular aspect, the containment flaps 126 and 128 extend the entire length of the absorbent core 112 to better contain the body exudates. Containment flaps are generally well known to those skilled in the art. For example, suitable constructions and arrangements for containment flaps are described in U.S. Pat. No. 4,704,116 issued Nov. 3, 1987 to K. Enloe, the disclosure of which is hereby incorporated by reference in a manner consistent with the present document.

Referring now to FIG. 3, there is shown ears 138 and 140 (also commonly referred to as tabs or side panels) which are adhesively attached to diaper 101. Typically, the ears 138 and 140 are separately formed and attached to the outer cover, to the bodyside liner, between the outer cover and the bodyside liner, or to other suitable components located in the ear attachment zone of the diaper. The ears 138 and 140 may be elastic or otherwise rendered elastomeric. For example, the ears 138 and 140 may be an elastomeric material such as a neck-bonded laminate (NBL) or stretch-bonded laminate (SBL) material. Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987 in the names of Taylor et al., the disclosures of which are hereby incorporated by reference in a manner consistent with the present document. Examples of articles that include elasticized side panels and selectively configured fastener tabs are described in U.S. Pat. No. 5,496,298 issued Mar. 5, 1996 to Kuepper et al.; U.S. Pat. No. 5,540,796 to Fries; and U.S. Pat. No. 5,595,618 to Fries; the disclosures of which are also incorporated herein by reference in a manner consistent with the present document. Alternatively, the ears 138 and 140 may be formed integrally with a selected diaper component. For example, the ears 138 and 140 can be integrally formed with the inner or outer layer of the outer cover or may be integrally formed from with the bodyside liner.

Fastening components, such as hook fasteners 142 and 144 are typically employed on the ears 138 and 140 to secure the diaper 101 on the body of a child or other wearer by connecting the ears 138 and 140 to the pub patch (loop fastener) previously described. The hook fasteners 142 and 144 are adhesively bonded (not shown) to the ears 138 and 140. Alternatively, other fastening components (not shown), such as buttons, pins, snaps, adhesive tape fasteners, cohesives, mushroom-and-loop fasteners, or the like, may be employed. Desirably, the interconnection of the fastening components is selectively releasable and re-attachable. In the illustrated embodiment, the hook fasteners 142 and 144 are attached to and extend laterally out from the respective ears 138 and 140 at the back region of the diaper 101.

To provide improved fit and to help further reduce leakage of body exudates from the diaper 101, elastic components are typically incorporated into the diaper 101, particularly at the waist area and the leg areas. For example, as illustrated in FIG. 3, the diaper 101 has a waist elastic component 132 and leg elastics 134 and 136. The waist elastic 132 is configured to gather and shirr the end margins of the diaper 101 to provide a resilient, comfortable close fit around the waist of the wearer.

The leg elastic components are typically secured between the outer and inner layers of the outer cover, such as by being bonded to one or both layers by a laminate adhesive. It should be understood, however, that the leg elastic components may be secured between the outer and inner layers of the outer cover by other methods.

Each elastic component generally comprises an elongate substrate, such as a sheet or ribbon, having threads or strands of elastic material secured to the substrate in generally parallel, spaced relationship with each other. As an example, one suitable elastic material from which the elastic strands may be constructed is a dry-spun coalesced multi-filament elastomeric thread sold under the trade name LYCRA and available from E.I. du Pont de Nemours (Wilmington, Del.). The elastic strands are desirably secured to the substrate while in a stretched condition such that the retractive forces of the elastic strands tend to gather the substrate. The substrate is in turn secured to the bodyside liner 124 which is turn is attached to the outer cover 100 with the substrate ungathered such that the retrative forces of the elastic strands gather the diaper at the leg openings to provide a snug fit around the wearer's leg. The various components of the diaper 101 are integrally assembled together using a suitable form of attachment, such as a combination of adhesives, sonic bonds, thermal bonds.

Examples of other diaper configurations suitable for use in connection with the instant application that may or may not include diaper components similar to those described previously are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996 to Hanson et al., the disclosures of which are hereby incorporated by reference in a manner consistent with this document.

To insure that the articles described above are assembled accurately, it is desirable to control the physical properties of the materials during the assembly process. For instance, the failure to deliver a web of constant strain of certain materials during the assembly process can affect the relative placement of components on the web, which can result in a defective product. As noted above, the liquid permeable outer layer 102, the body sideliner 124, the absorbent core 112, and various loop materials may each be part of a web, the strain of which may effect their placement. Thus, by using a control scheme to control web strain variability, the number of defective products produced during the assembly process can be reduced significantly.

Figure 4:
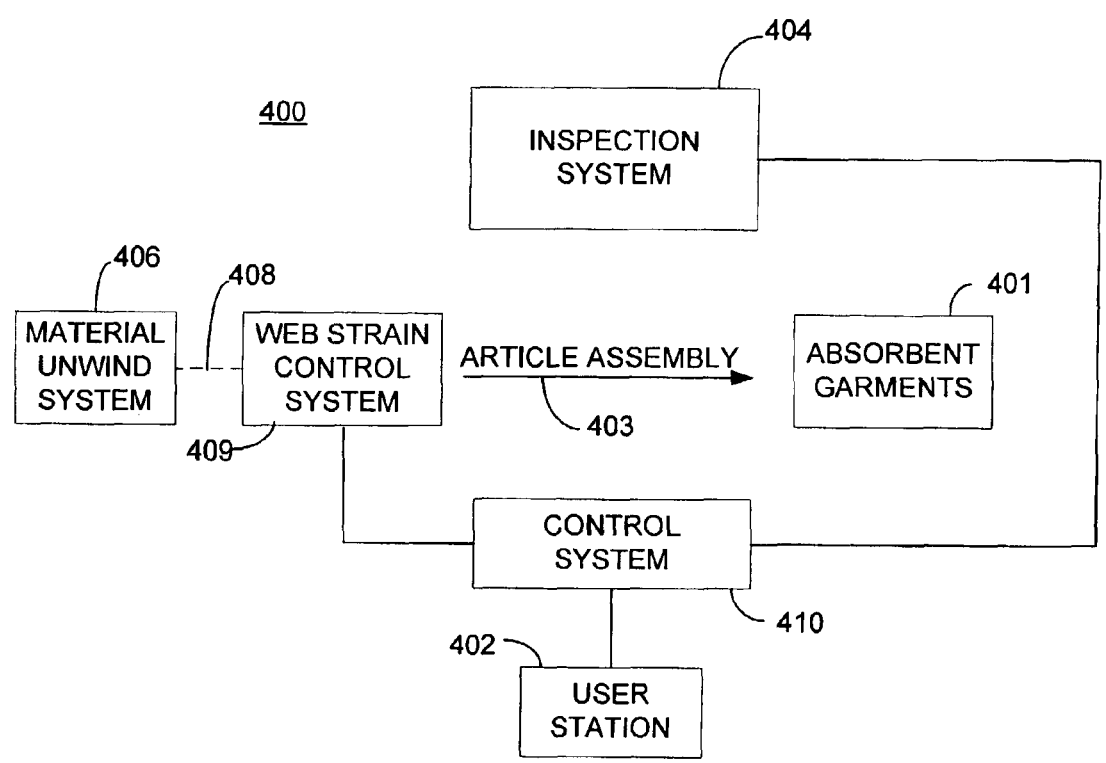
FIG. 4 is a block diagram illustrating a system for assembling pre-fastened articles such as absorbent garments.

Referring now to FIG. 4, a block diagram illustrates a control system 400 that may be used for assembling articles such as absorbent garments such as the diaper 101 illustrated in FIGS. 1–3. A user station 402 and a manufacturing control system 410 control and monitor the assembly of absorbent garments 401 during an article assembly process, indicated by reference character 403. An inspection system 404 may be employed to examine the assembled absorbent garments and detect and/or segregate defective absorbent garments. A material unwind system 406 retrieves and supplies a web material 408 to the assembly process at a substantially constant tension. An example of such an unwind system is described in U.S. Pat. No. 6,473,669 entitled CONTROLLING WEB TENSION, AND ACCUMULATING LENGTHS OF WEB, BY ACTIVELY CONTROLLING VELOCITY AND ACCELERATION OF A FESTOON, by Rajala et al., the entire disclosure of which is incorporated herein by reference in a manner consistent with the present document. Finally, a web strain control system 409 that is responsive to web control information for further maintaining the web material 408 delivered to the assembly process at a substantially constant strain may be included in the system 400. The manufacturing control system 410 is responsive to the inspection system 404, the web strain control system 409, and the user station 402. The web strain control system 409 may employ control system 410, as illustrated, or it may have its own control system as will be described below in greater detail (see FIG. 7). As illustrated in FIG. 4, the web strain control system 409 is located at the front end of the article assembly process 403. Consequently, the web control system 409 affects the article assembly process 403, and can affect what is detected by the inspection system 404 and can affect the quality of the absorbent garments 401 produced by the system 400. Thus, an invention directed toward web strain control during the article assembly process can be particularly instrumental in improving the quality of the absorbent garments 401 produced therefrom.

Figure 5:
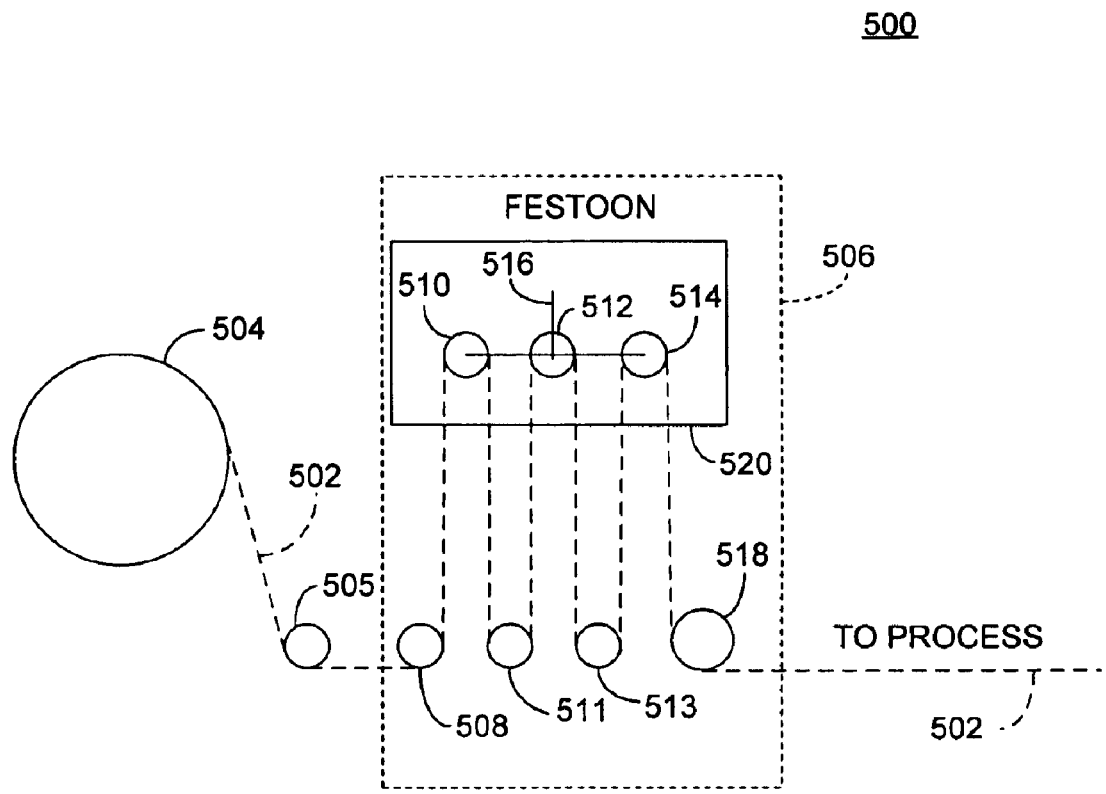
FIG. 5 is a block diagram illustrating a conventional unwind control system 500 for controlling a web material 502 supplied to a manufacturing process.

Referring now to FIG. 5, a conventional unwind control system 500 for controlling a web material 502 supplied to a manufacturing process is illustrated. An unwind roller 504 in combination with the speed of a lower intake roller 505 of a festoon 506 controls the speed at which the web material 502 advances toward the festoon 506. The web 502 then enters the festoon 506 at turning roll 508, passes over turning roll 508, and from there enters the festoon 506, itself. The festoon 506 includes upper festoon rolls 510, 512, 514, lower festoon rolls 511, 513, and coupler 516. The web 502 departs the festoon 506 at turning roll 518 and passes out of the festoon 506 upon departing turning roll 518. Between rolls 508 and 518, the festoon 506 controls both tension in the web 502 and the length of web 502 accumulated in the festoon 506. The festoon 506 accumulates web 502 so web material 502 can continue to be fed to the manufacturing process while the intake roller 505 is stopped and a splice is being made from one roll of raw material to another.

The upper festoon rolls 510, 512, 514 are coupled together by the coupling 516 for common vertically movement within an operating window 520 defined between the fixedly mounted lower turning rolls and upper turning pulleys in a endless cable system. The endless cable system may be a system such as described in the above referenced U.S. Pat. No. 6,473,669. One or more position transducers (not shown) sense the position of the upper festoon rolls 510, 512, 514 within in the operating window. A generally static force having a vertical component is provided to the upper festoon rolls 510, 512, 514 by a loading element (not shown) such as an air cylinder. Variable forces, such as described in the above referenced U.S. Pat. No. 6,473,669, are applied by a controller (not shown) to coupling 516 to control web tension and the length of web 502 accumulated in the festoon.

While generally successful, the present invention provides an alternative approach that may be advantageous during speed transients such as splice operations and process stops and starts.

Figure 6:
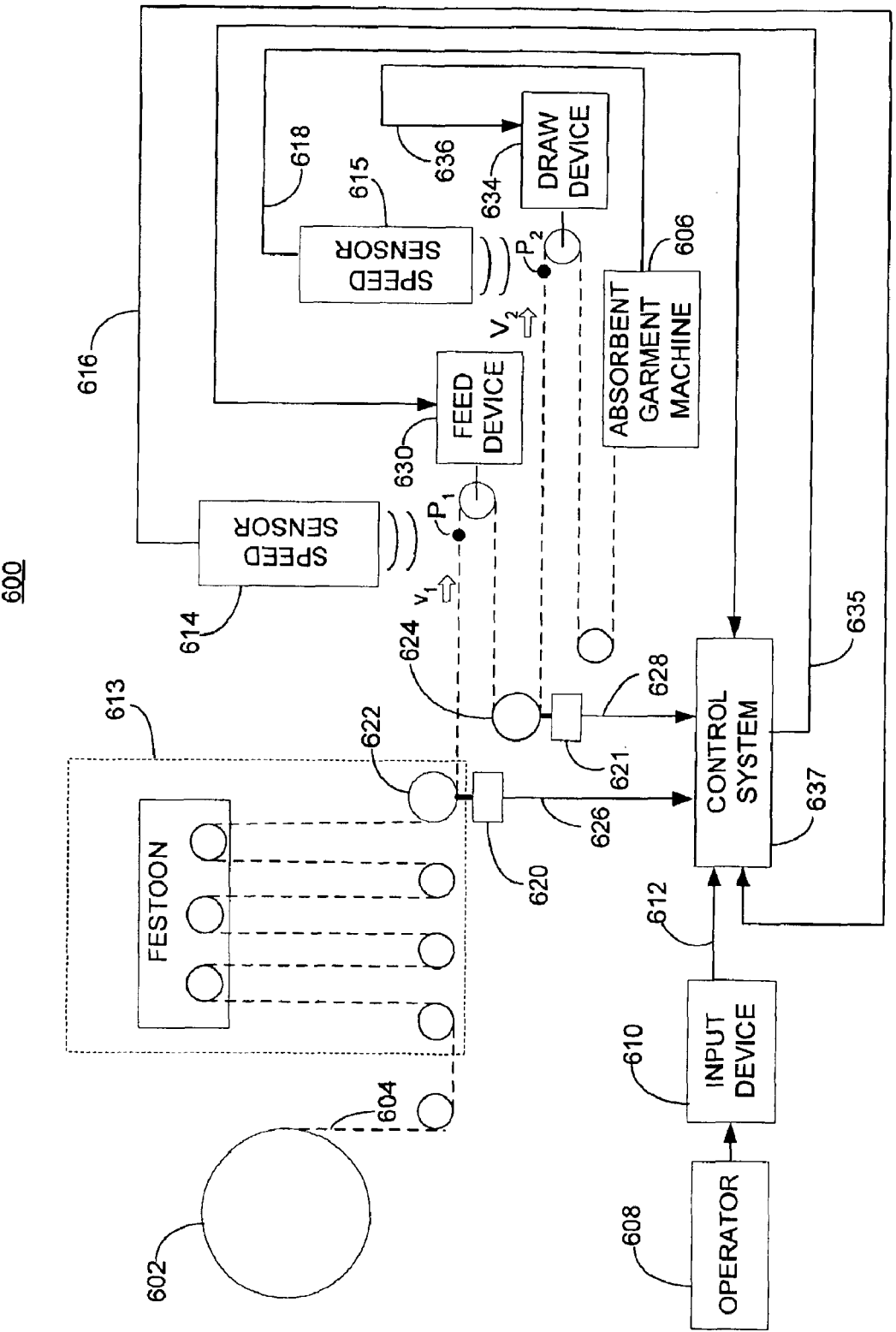
FIG. 6 is an exemplary block diagram illustrating the components of a system and method according to a particular embodiment of the invention.

Referring now to FIG. 6, an exemplary block diagram illustrates a system 600 for controlling the strain of a material supplied from a material unwind 602 to form a web 604 during a manufacturing process of an article, such as an absorbent garment manufactured by an absorbent garment manufacturing machine 606.

In one embodiment, an operator 608 uses an input device 610 to define a target strain for the web 604. In this case, the input device 610 is a computer keyboard associated with a personal computer (PC) system that controls and monitors a force being applied to the web 604. In another embodiment (not shown), the target strain information is automatically retrieved from a manufacturing database by the PC system that controls and monitors the force being applied to the web 604. The operator 608 using the input device 610 defines a desired target strain of web 604 based on previous experiences or based on information the operator 608 retrieves from manufacturing reference manuals. For example, the operator 608 may refer to a manufacturing reference manual and determine a target strain for the web 604 based on the particular type of absorbent garment which will be fabricated from the web 604. Such target web strains may, for example, vary from 0.5% to 6%. As a particular example, the operator 608 uses the input device 610 to enter a determined strain of 1%. In another embodiment, the operator 608 may use the input device 610 to define a target range for the strain of the web 604 rather than a specific target strain. For instance, the operator 608 uses a computer keyboard to enter keystrokes that define upper and lower limits for the strain of web 604. Consequently, the upper and lower limits define a range of web strains that are acceptable during the manufacture of a particular absorbent garment. For example, the upper and lower limits may be defined as 0.75% and 1.25% respectively. Notably, a particular target strain is a specific example of a target range. After the operator 608 enters the target strain information, the input device 610 generates a reference signal 612. The reference signal 612 can be in a digital format or an analog format. For example, if the operator 608 uses a computer keyboard as the input device 610, the reference signal 612 will be generated in a digital format. Alternatively, if the operator 608 uses a potentiometer as the input device 610, the reference signal 612 is generated in an analog format. In this latter embodiment, the reference signal 612 is a voltage having a magnitude corresponding to the target strain of the web 604.

A tensioning device 613, such as the festoon described above in reference to FIG. 5, controls the tension in the web 604 traveling along a path from the unwind 602 to the machine 606. The tensioning device 613 is located along the path of the web 604 and upstream of the system 600 controlling the strain of the web 604. Although the invention is described herein in conjunction with a festoon, the invention can be used in conjunction with any other loading device 613 used for applying tension to a web 604. For example, another method for controlling tension of a web 604 involves the use of a dancer bar such as described in the above referenced U.S. Pat. No. 6,473,669.

Speed sensors 614, 615 are used for sensing the speed of the web 604 as it travels along the path during the manufacturing process. More specifically, speed sensor 614 senses a first speed $V_1$ of the web 604 at a first position $P_1$ along the path and speed sensor 615 senses a second speed $V_2$ of the web 604 at a second position $P_2$ along the path. In one embodiment, the speed sensors 614, 615 are laser doppler speed detectors such as TSI Model LS200 Laser-Speed® Noncontact Length and Speed Gauges manufactured by TSI Incorporated, a business having offices located in Shoreview, Minn. In response to sensing the first speed $V_1$ and the second speed $V_2$, speed sensors 614, 615 generate a first speed signal 616 and a second speed signal 618, respectively. In this embodiment, speed signals 616, 618 are generated in digital format. However, speed signals 616, 618 can also be analog voltage signals having magnitudes corresponding to the respective sensed speed. Although the example of the speed sensor 614 described herein includes a laser doppler speed detector, the speed sensor 614 is not limited to such an embodiment and can include any speed sensor 614 known to those skilled in the art.

Tension sensors 620, 621 sense the tension of the web 604 as it travels along a path during the manufacturing process. Tension sensor 620 senses a first tension $T_1$ of the web 604 via a web guide 622 engaging the web upstream of the first position $P_1$ along the path. Tension sensor 621 senses a second tension $T_2$ of the web 604 via a web guide 624 engaging the web downstream of the first position $P_1$ along the path. As used herein, the terms upstream and downstream are used to define locations of first and second points along a web traveling along a path and having a web direction, a first point at a first location at the start of the path, and a second point further along the defined web in the web traveling direction relative to the first point at a second location. That is, the first point is upstream from the second point, and the second point is downstream from the first point. In one embodiment, the tension sensors 620, 621 are MAGPOWR® model TS load cells manufactured by Magnetic Power Systems, Inc. In response to sensing the first tension $T_1$ and the second tension $T_2$, tension sensors 620, 621 generate a first tension signal 626 and a second tension signal 628, respectively. Tension signals 626, 628 are generated in analog format. For example, the generated tension signal can range from 0 to 10 volts. However, tension signals 626, 628 can also be digital signals having magnitudes corresponding to the respective sensed tension. (grams: e.g. 0 to 500)

A feed device 630 controls the strain of the web 604 being supplied to the manufacturing process. More specifically, the feed device 630 controls the speed at which the web 604 travels along the path from the feed device 630 to a draw device 634; which corresponds to the speed of the web 604 at the first position $P_1$ along the path. The draw device 634 controls the speed at which the web 604 travels along the path from the draw device 634 to the machine 606 receiving the web 604; which corresponds to the speed of the web 604 at the second position $P_2$ along the path. The draw device 634 maintains the speed of the web 604 from the draw device 634 to the machine 606 substantially fixed relative to the process speed (i.e., line speed of the machine 606).

In contrast, the feed device 630 can supply the web 604 to the draw device 634 at variable speeds relative to the process speed. The feed device 630 is responsive to a speed control signal 635 to vary the speed at which the web 604 travels towards the draw device 634 to maintain the strain of the web 604 within the target range or at the target strain as defined by the operator 608 via the input device 610. In one such embodiment, the feed device 630 includes a motor driven feed roller and the draw device 634 includes a motor driven draw roller such as described below in reference to FIG. 7. The feed device 630 varies the strain of the web 604 between the feed device 630 and the draw device 634 by adjusting the speed of the web 604 at the first position $P_1$ relative to the speed of the web 604 at the second position $P_2$.

For example, when a determined strain of the web 604 is less than the target strain for the web 604 the speed control signal 635 applied to the feed device 630 decreases the speed of the web 604 at the first position $P_1$ relative to the speed of the web 604 at the second position $P_2$. The decreased speed of the web 604 at the first position $P_1$ relative to the speed of the web 604 at the second position $P_2$ increases a tension in the web 604 such that the web 604 stretches an amount along its length between the first position $P_1$ and the second position $P_2$. The elongation in length of the web 604 between the first position $P_1$ and the second position $P_2$ causes the strain of web 604 to increase to an amount until the web strain as calculated by a control system (see below) is within or at the target strain.

Alternatively, when the determined strain of the web 604 is greater than the target strain for web 604, the speed control signal 635 applied to the feed device 630 increases the speed of the web 604 at the first position $P_1$ relative to the speed of the web 604 at second position $P_2$. The increased speed of the web 604 at the first position $P_1$ relative to the speed of the web 604 at second position $P_2$ decreases a tension in the web 604 such that the stretch of web 604 reduces an amount along its length between first position $P_1$ and the second position $P_2$. The reduced stretch of the web 604 causes the strain of web 604 to decrease to an amount until the web strain as calculated by the control system (see below) is within or at the target strain. The draw device 634 is responsive to a machine reference signal 636 to maintain the speed of the web 604 at the second position $P_2$ substantially fixed relative to the process speed (i.e., line speed of the machine 606). For example, the machine 606 may generate a reference signal 636 that is representative of a line speed at which the machine 606 is operating. The reference signal 636 can be provided to the draw device such that the web speed at the second position $P_2$ is substantially fixed relative to the line speed off the machine 606.

Strain is defined as the amount of deflection per unit of an initial sample length (i.e., percentage). In this case, the web has a first strain upstream further along the defined web path in the web traveling direction relative to the first position $P_1$ and a second strain downstream along the defined web path opposite the web traveling direction relative to the of the first position $P_1$. The change in strain from first strain upstream of the first position $P_1$ to the second strain downstream of the first position $P_1$ can be calculated by the following equation:

$$\in_2 - \in_1 = \Delta L / L_o; \qquad (1)$$

where $\Delta L$ is the change in length of a sample length of the web 604, $L_o$ is the initial sample length of the web 604, $\in_1$ is the strain of the web 604 upstream of the first position $P_1$, and $\in_2$ is the strain of the web 604 downstream of the first position $P_1$ and corresponds to the strain of the web 602 controlled by the system 600 and supplied to the machine 606.

The strain of a material such as a web 604 can also be determined as a function of its modulus of elasticity. The modulus of a material is defined as the slope of the material's stress strain curve and can be defined by the following equation:

$$E = \sigma / \in; \tag{2}$$

where $\sigma$ is material stress, $\in$ is material strain, and E is the modulus of elasticity.

Stress is the amount of load per unit area and can be calculated by the following equation:

$$\sigma = F/A; \tag{3}$$

where F is the force applied to the web, and A is the cross-sectional area of web. Because measuring the thickness of the web 604 can be impractical, the area of the web 604 may be defined as equal to the width of the web, and because tension is a force applied to the web, the following equation can be derived from equation 3:

$$\sigma = T/W; \tag{4}$$

where T is the tension of the web, and W is the width of the web.

By combing equations 2, 3 and 4 the first strain $\in_1$ can be determined as a function of the first tension $T_1$ sensed by the tension sensor 620 and can be calculated by the following equation:

$$\in_1 = T_1 / E \cdot W. \tag{5}$$

Likewise, the second strain, $\in_2$, can be determined as a function of the second tension $T_2$ sensed by the tension sensor 621 and can be calculated by the following equation:

$$\in_2 = T_2 / E \cdot W. \tag{6}$$

In this instance, for calculation and control purposes, the web width, W, is assumed to be constant along the path of the web 604. More specifically, any change between the width of the web downstream of the first position $P_1$ and the width of web upstream of first position $P_1$ is assumed to have a negligible effect on the second strain. Generally, unwinds 602 of web material are provide a web 604 within a certain width specification. Thus, the width of the web 604 on a given unwind 602 typically varies only an incidental amount. In alternate embodiment (not shown), width sensors may be position along the path of the web to determine the width of web downstream of the first position and the width of the web upstream of the first position.

As described above, the change in length ΔL of the web 604 corresponds to the speed differential of the web 604 between the first position $P_1$ and the second position $P_2$. For example, decreasing the speed of the web 604 at the first position $P_1$ relative to the speed of the web 604 at the second position $P_2$ increases the tension of the web 604 along the path between $P_1$ and $P_2$. The increased tension between $P_1$ and $P_2$ increases the length of the web 604 between $P_1$ and $P_2$. Alternatively, increasing the speed of the web 604 at the first position $P_1$ relative to the speed of the web 604 at the second position $P_2$ decreases the tension of the web 604 between $P_1$ and $P_2$. The decreased tension between $P_1$ and $P_2$ decrease the length of the web 604 between $P_1$ and $P_2$. The following equation illustrates a relationship between the sensed speeds $V_1$, $V_2$ and the change in length ΔL:

$$\Delta L = (V_1 31 \ V_2)/t \tag{7}$$

where $V_1$ is the speed of the web 604 sensed at the first position $P_1$, $V_2$ is the speed of the web 604 sensed at the second position $P_2$, and t is the time increment. In addition, the length $L_o$ of the web 604 that initially enters the span over a defined time period defines the initial length of the web 604 within the defined span and can be determined by the following equation.

$$L_o = V_1 \cdot t. \tag{8}$$

By combining equations 1, 7 and 8 the following equation can be derived and used to determine the change in the strain of the web 604 from the first position to the second position:

$$\in_2 - \in_1 = (V_2 - V_1)/V_1. \tag{9}$$

Generally, the speed and tension of the web 604 can be sensed, but the stress, strain, and modulus of the web 604 are unknown and are calculated. However, by combining equations 5, 6 and 9, the following equations can be derived and used to determine the first strain and the second strain of the web:

$$\in_1 = [(V_2 - V_1)/V_1] \cdot [T_1/(T_2 - T_1)]; \tag{10}$$

$$\in_2 = [(V_2 - V_1)/V_1] \cdot [T_2/(T_2 - T_1)]. \tag{11}$$

A control system 637 is linked to the input device 610, speed sensors 614, 615 and tension sensors 620, 621 to receive the reference signal 612 speed signals 616, 618, and tension signals 626, 628. The control system 637 can be a control circuit, a computer that executes control software, or a programmable logic controller such as such as a RELIANCE® AUTOMAX® Controller manufactured by Rockwell Automation, a business having offices located in Mayfield Heights, Ohio. In this embodiment, the control system 637 determines the first strain of the web 604 and the second strain of the web 604 as a function of tensions $T_1$, $T_2$ as indicated by tension signals 626, 628 and speeds $V_1$, $V_2$ as indicated by speed signals 616, 618. In this case, the control system 637 determines the first strain by executing an algorithm that employs the relationships defined in equation 10, and determines the second strain by executing an algorithm that employs the relationships defined in equation 11.

The control system 637 compares the determined second strain to the target strain as indicated by the reference signal 612. If the determined second strain is not equal to the target strain, or within the target strain range, the control system generates the speed control signal 635 as a function of the target strain as indicated by reference signal 612, the second speed as indicated by speed signal 618, and the determined first strain. The generated speed control signal 635 determines how the feed device 630 will adjust the speed of the web 604 at the first position $P_1$. For example, a determined strain that is lower than the desired target strain represented by the reference signal 612 indicates that the strain of the web 604 should be increased. In order to increase the strain of web 604, the speed control signal 635 can produce a decrease in the first speed $V_1$ of the web 604 relative to the second speed $V_2$ of the web 604. Alternatively, a determined strain which is greater than the desired target strain represented by the reference signal 612 means that the strain of the web 604 should be decreased. In order to decrease the strain of the web 604, the speed control signal 635 can produce an increase in the first speed $V_1$ of the web 604 relative to the second speed $V_2$ of the web. Hence, the output of control system 637 applies the speed control signal 635 to the feed device 630 to achieve the desired web strain.

The speed control signal 635 is representative of a target speed for the web 604 at the first position $P_1$. In one embodiment, the control system 637 executes an algorithm that calculates the target speed as function of the target strain as indicated by reference signal 612, the speed sensed at the second position as indicated by speed signal 618, and a determined first strain. For example, the control system 637 executes an algorithm that calculates the target speed by using the following equation derived from equation 9:

$$V_T = V_2/(\in_T - \in_1 + 1); \quad (12)$$

where $V_T$ is the target speed (i.e., $V_1 = VT$), $\in_T$ is the target strain (i.e., $\in_2 = \in_T$), and $E_1$ is the determined first strain. Thus, the control system 637 provides the speed control signal 635 to the feed device 630 to produce the target speed $V_T$ of the web 604 at the first position $P_1$ to achieve the target strain as defined by the operator 608 via the input device 610.

Figure 7:
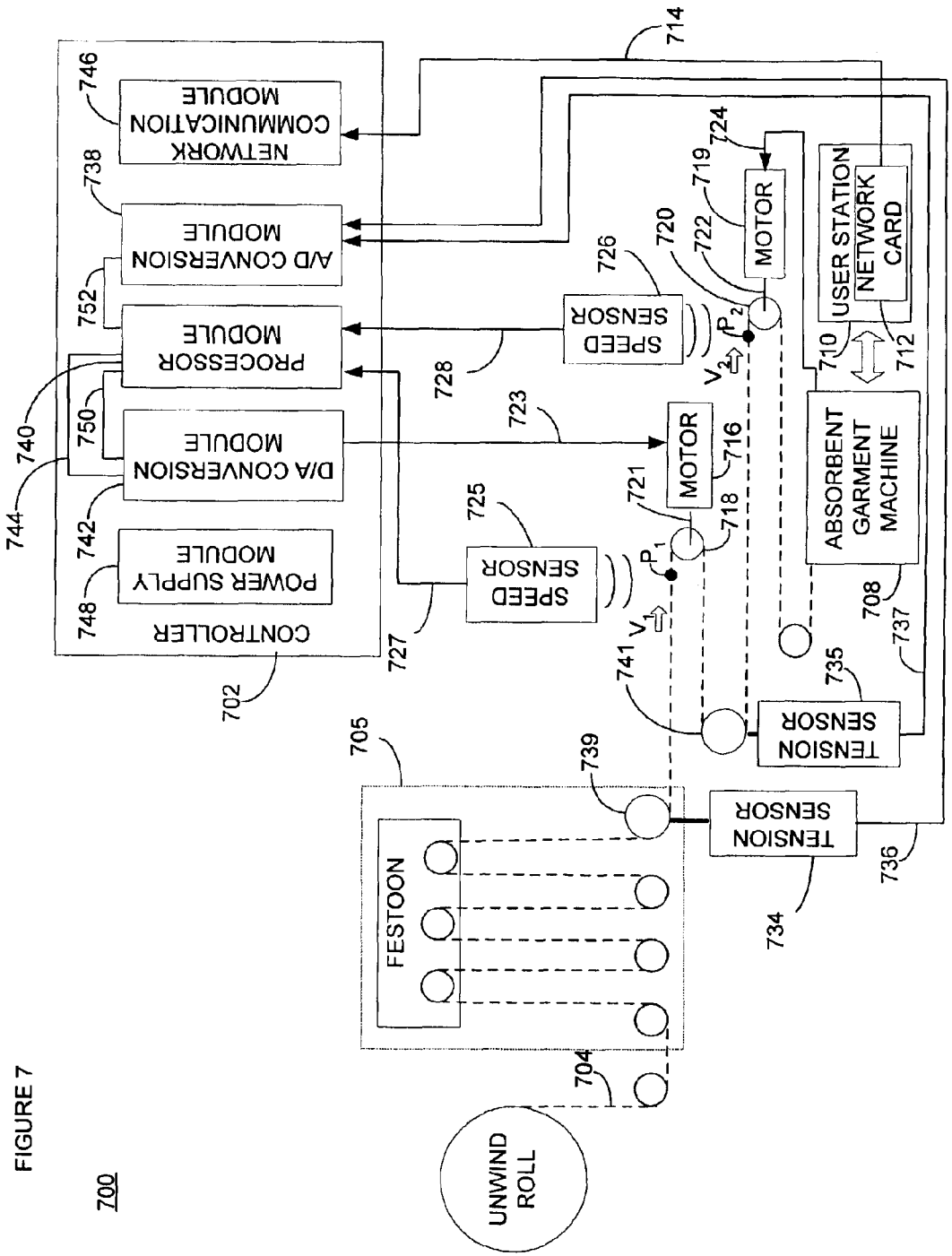
FIG. 7 is an exemplary block diagram illustrating a system including a controller for controlling the strain of the web supplied to an absorbent garment manufacturing machine.

Referring now to FIG. 7, an exemplary block diagram illustrates a system 700 including a controller 702 to control the strain of a web 704 supplied from a loading device 705 to an absorbent garment-manufacturing machine 708 that manufactures absorbent garments.

A user station 710 controls and monitors the manufacture of absorbent garments on the absorbent garment-manufacturing machine 708. In one embodiment, the user station 710 is a personal computer (PC) system. As described in reference to FIG. 6, an operator can use a keyboard associated with the PC system to define a target strain for the web 704 and generate a reference signal. In one embodiment, the user station 710 is associated with a computer network and includes a network interface card 712 for communicating with other network devices. In such an embodiment, after the operator defines the target strain for the web 704, the operator uses the user station 710 to communicate the reference signal to another network device such as the controller 702 via a link 714.

A first motor 716 drives a feed roller 718 that controls the speed of the web 704 at a first position $P_1$. A second motor 719 drives a feed roller 720 that controls the speed of the web 704 at a second position $P_2$. The feed roller 718 is mechanically linked to a rotor 721 of the first motor 716 such that when the first motor 716 is activated, it rotates the rotor 721, which causes the feed roller 718 to rotate. The draw roller 720 is mechanically linked to a rotor 722 of the second motor 719 such that when the second motor 719 is activated, it rotates the rotor 722, which causes the feed roller 718 to rotate. The first motor 716 is responsive to a speed control signal 723 to adjust the rotational speed of the feed roller 718. The second motor 719 is responsive to a machine reference signal 724 to maintain the rotational speed of the draw roller 720 substantially fixed relative to the line speed of the machine 708.

In this case, the first motor 716 is responsive to the speed control signal 723 to adjust rotational speed of the feed roller 718 relative to the rotational speed of the draw roller 720 and, thus, adjust the strain of the web 704. For example, when the strain of the web 704 is determined to be less than the target strain for the web 704, the first motor 716 decreases the rotational speed of the feed roller 718 an amount relative to the rotational speed of the draw roller 720. The decreased rotational speed of the feed roller 718 translates into a decreased speed of the web 704 at the first position $P_1$ relative to the speed of the web 704 at second position $P_2$. The decreased speed of the web 704 at the first position $P_1$ relative to the speed of the web 704 at the second position $P_2$ increases a tension in the web 704 such that the web 704 stretches an amount along its length between $P_1$ and $P_2$. The elongation in length of the web 704 between the first position $P_1$ and the second position $P_2$ causes the strain of web 704 to increase to an amount until the web strain as calculated by a control system (see below) is within or at the target strain. Alternatively, when the determined strain of the web 704 is greater than the target strain for web 704, the speed control signal 723 applied to the first motor 718 increases the rotational speed of the feed roller 719 relative to the rotational speed of the draw roller 720. The increased rotational speed of the feed roller 718 translates into an increased speed of the web 704 at the first position $P_1$ relative to the speed of the web 704 at second position $P_2$. The increased speed of the web 704 at the first position $P_1$ relative to the speed of the web 704 at second position $P_2$ decreases a tension in the web 704 such that the stretch of web 704 reduces an amount along its length between $P_1$ and $P_2$. The reduced stretch of the web 704 causes the strain of web 704 to decrease to an amount until the web strain as calculated by the control system (see below) is within or at the target strain.

Speed sensors 725, 726 are used to generate digital speed signals 727, 728, respectively. In this embodiment, the speed sensor 725 detects a speed of the web 704 at the first position $P_1$ along the path of the web 704 and speed sensor 726 detects the speed of the web 704 at the second position $P_2$ along the path of the web 704. Thus, the digital speed signals 727, 728 are representative of the speed of the web 704 at the first position $P_1$ along the path of the web 704 and the speed of the web 704 at the second position $P_2$ along the path of the web 704.

Tension sensors 734, 735 are used to generate analog tension signals 736, 737 respectively. In this embodiment, the tension sensor 734 detects a tension force applied to the web 704 upstream of the first position $P_1$ along the path of the web 704. Tension sensor 735 detects the tension force of the web 704 downstream of the second position $P_2$ along the path of the web 704. Thus, analog tension signals 736, 737 are representative of the tension force applied to the web 704 upstream of the first position $P_1$ along the path of the web 704 and the tension force applied to the web 704 downstream of the second position $P_2$ along the path of the web 704, respectively. In this embodiment, tension sensor 734 includes a web guide or roller 739 that engages the web 704, to detect the tension force upstream of the first position $P_1$. Tension sensor 735 includes a web guide or roller 741 that engages the web 704 to detect the tension downstream of the first position $P_1$.

Analog tension signals 736, 737 are provided to an analog to digital conversion module 738 of controller 702 which converts the analog signals to corresponding digital signals which are provided to a processor module 640 of the controller 702.

Digital speed signals 727, 728 are provided directly to processor module 740 of the controller 702. The processor module 740 calculates the strain of the web 704 and compares it to the target strain as indicated to the network card 712 via a link 714. Depending on the comparison, the processor module 740 provides a digital signal representative of a target speed of the web 704 at the first position $P_1$. For example, if the calculated strain is greater than the target strain, the speed of the web at the first position $P_1$ can be increased so that digital signal would have a decreased digital value. As another example, if the calculated strain is less than the target strain, the speed of the web 704 at the first position $P_1$ can be decreased so that digital signal would have an increased digital value. In this instance, the processor module 740 calculates the target speed for the web 704 at the first position $P_1$ and generates the digital signal as a function of the calculated strain, the target strain as indicated by the digital reference signal, and the speed of the web 704 at the second position $P_2$ as indicated by the digital speed signal 728. The generated digital signal is provided via link 744 to a digital to analog conversion module 742 which converts the digital signal into a corresponding analog signal provided as the speed control signal 723.

In this embodiment, the first motor 716 receives the speed control signal 723 from the controller 702 and is used to increase or decrease the rotational speed of the feed roller 718 as described above.

In one embodiment, the controller 702 is a programmable logic controller (PLC) such as a RELIANCE® AUTOMAX® Controller manufactured by Rockwell Automation that can be programmed to control a process or machine operation. In such an embodiment, the controller 702 contains areas or slots where input/output (I/O) modules (i.e., racks) can be connected directly to the controller 702. The I/O modules serve as the interface through which input and output devices are connected. In other words, the input devices provide input signals to the controller 702 via the I/O modules and the output devices receive output signals from the controller 702 via the I/O modules. In this instance, the user station 710, tension sensors 734, 735 and speed sensors 725, 726 are input devices and the first motor 716 is an output device. In this embodiment, the I/O modules include a network communications module 746, a digital to analog conversion module 742, an analog to digital conversion module 738, a processor module 740, and a power supply module 748. The network communications module 746 allows the controller 702 to communicate with other network devices and with other I/O modules in the controller 702. The digital to analog conversion module 742 converts signals from a digital format to an analog format. The analog to digital conversion module 738 converts signals from an analog format to a digital format. The processor module 740 receives digital input, and is programmable for generating a digital output as a function of the digital input. A power supply module 748 regulates and supplies power to the modules of the controller 702.

In operation, the operator uses the user station 710 to define a target web strain. The user station 710 generates a digital reference signal representative of the target web strain that is transferred to the network communications module 746 via the network card 712 and link 714. The network communications module 746 communicates the digital reference signal to the processor module 740 via a link 750. Speed sensor 725 detects the speed of the web 704 at the first position $P_1$ and produces digital speed signal 727 that is representative of the detected speed. Speed sensor 726 detects the speed of the web 704 at the second position $P_2$ and produces digital speed signal 728 that is representative of the detected speed. The digital speed signals 727, 728 are provided to the processor module 740 of the controller 702. Tension sensor 734 detects the tension force applied to the web 704 upstream of the first position $P_1$ and produces analog tension signal 736 that is representative of the detected tension force. Tension sensor 735 detects the tension force applied to the web 704 downstream of the first position $P_1$ and produces analog tension signal 737 that is representative of the detected tension force. The analog tension signals 736, 737 are provided to the analog to digital conversion module 738 of the controller 702. The analog to digital conversion module 738 converts the analog tension signals 736, 737 to digital tension signals. The analog to digital conversion module 738 provides the digital tension signals to the processor module 740 via a link 752. The processor module 740 calculates a first strain of the web 704 upstream of the first position $P_1$ as a function of the first and second speeds as indicated by digital speed signals 727, 728, and first and second tensions as indicated by digital tension signals via link 752. (e.g., see equation 10). The processor module 740 calculates a second strain of the web 704 downstream of the of the first position $P_1$ as a function of the first and second speeds as indicated by digital speed signals 727, 728, and first and second tensions as indicated by digital tension signals via link 752. (e.g., equation 11). The processor module 740 compares the calculated second strain to the desired strain as indicated by digital reference signal and determines whether to generate a digital speed control signal. To generate the digital speed control signal, the processor module 740 calculates the target speed of the web 704 at the first position $P_1$ as a function of the calculated first strain, the target strain as indicated by the digital reference signal via link 714, and the speed of the web 704 at the second position $P_2$ as indicated by the digital speed signal 728. The processor module 740 provides the digital speed control signal to the digital to analog conversion module 742 via link 744. Links 744, 750 and 752 may be a bus. The digital to analog conversion module 738 converts the digital speed control signal to the analog speed control signal 723. The analog speed control signal 723 is applied to the first motor 716 to vary the rotational speed of the feed roller 718. The rotational speed of feed roller 718 increases or decreases relative to the rotational speed of the draw roller 720 to vary the tension force applied to the web 704. For example, the rotational speed of the feed roller 718 is decreased to increase the tension force applied to the web 704 when the comparison between the digital reference signal and the calculated strain indicates the web strain is less than the target strain. Alternatively, the rotational speed of the feed roller 718 is increased to decrease the tension force applied to the web 604 when the comparison between the digital reference signals and digital feedback signal indicates the web strain is greater than the target strain.

In one embodiment, the user station 710 contains control software such as AUTOMAX® Programming Executive available from Rockwell Automation, which can be used for configuring the processor module 740 to execute algorithms that employ equation 10, equation 11 and/or equation 12 to generate the analog speed control signal 723.

Referring now to FIG. 8, an exemplary flow chart illustrates a method for managing a manufacturing processing operation according to exemplary embodiment described in reference to FIG. 6. At step 802, operator 608 uses input device 610 to define the target web strain and generate reference signal 612 that is representative of the target web strain as defined by operator 608 via input device 610. At step 804, the speed sensors 614, 615 sense the speed of the web 604 at the first position $P_1$ and at the second position $P_2$ along the path of the web 604 being supplied to the manufacturing process and generate speed signals 616, 618 that are representative of the sensed speeds. At step 806, the tension sensors 620, 621 sense the tension force applied to the web 604 upstream of the first position $P_1$ and downstream of the first position $P_1$, and generate tension signals 626, 628 that are representative of the sensed tension forces. At step 808, the speed signals 616, 618 and the tension signals 626, 627 are used by the control system 637 to calculate web strain (e.g., See equations 10, 11). At step 810, the target web strain as indicated by reference signal 612 and the calculated web strained are compared and the speed control signal 635 is generated as a function of the difference. If the calculated strain of web 604 is greater than the target strain, the speed of the web 604 at the first position $P_1$ is increased relative to the speed of the web of the second position P$_2$ at step 812. If the calculated strain of web 604 is less than the target strain, the speed of the web 604 at the first position P$_1$ is decreased relative to the speed of the web 604 at the second position P$_2$ at alternative step 814. If step 810 determines that the calculated strain of the web 604 is equal to the target strain or range, the speed of the web at the first position P$_1$ is unchanged as indicated by step 816. Throughout the manufacturing process, step 810 and alternative steps 812, 814 or 816 may be repeated to maintain the web strain at or within the target web strain or range. Although FIG. 8 refers to a target strain, a target range is also contemplated. In this case, a target strain is a specific example of a target range.

When introducing elements of the present invention or the embodiment(s) thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A system for controlling a strain of a web material traveling along a path, the web material having a length between a first position along the path and a second position along the path, wherein the web material moves from the first position toward the second position, the system comprising an input device for indicating a target strain range;

a loading device positioned along the path upstream of the first position and engaging the web material for applying a first tension force to the web;

a feed device positioned along the path downstream of the loading device and engaging the web material for applying a second tension to the web by adjusting the speed of the web at the first position relative to the speed of the web at the second position in response to a speed control signal;

a first force sensor sensing the first tension force applied to the web material along the path upstream of the first position and a second force sensor sensing the second tension force applied to the web material along the path downstream of the first position;

a first speed sensor sensing a first speed of the web material at the first position along the path and a second speed sensor sensing a second speed of the web material at the second position along the path; and a control system for providing the speed control signal to the feed device as a function of the target strain range as indicated by the input device, the first tension force sensed by the first force sensor, the second tension force sensed by the second tension sensor, the first speed sensed by the first speed sensor and the second speed sensed by second speed sensor.

2. The system of claim 1, wherein the speed control signal provided by the control system maintains the strain of the web material within the target strain range as indicated by the input device.

3. The system of claim 1, wherein the input device generates a reference signal representative of a particular target strain for said web material, and wherein the control system generates the speed control signal as a function of the reference signal.

4. The system of claim 1, wherein the feed device is positioned along the path at or substantially near the first position, and wherein a draw device is positioned along the path at or substantially near the second position, wherein the feed device controls the first speed of the web at the first position along the path, and wherein the draw device controls the second speed of the web at the second position along the path.

5. The system of claim 4, wherein the feed device includes a feed roller that engages the web and rotates to impart the first speed of the web at the first position, and wherein the draw device is a draw roller that engages the web and rotates to impart the second speed of the web at the second position.

6. The system of claim 5, wherein a rotational speed of the teed roller determines the first speed of the web at the first position, and wherein a rotational speed of the draw roller determines the second speed of the web at the second position.

7. The system of claim 6, wherein the speed control signal is applied to the feed device to adjust the rotational speed of the feed roller relative to the rotational speed of the of the draw roller to apply the second tension force to the web material.

8. The system of claim 1, wherein the material has a first strain upstream of the first position and a second strain downstream of the first position, and wherein the control system provides the speed control signal to the feed roller to maintain the second strain of the web material within the target strain range as indicated by the input device.

9. The system of claim 8, wherein the control system determines the first strain, $\in_1$ and determines the second strain, $\in_2$, of the web material according to the following equations:

$$\in_1=[(V_2-V_1)/V_1]\cdot[T_2/(T_2-T_1)];$$
$$\in_2=[(V_2-V_1)/V_1]\cdot[T_2/(T_2-T_1)];$$

where $V_1$ is the speed of the web material sensed at the first position along the path, $V_2$ is the speed of the web material sensed at the second position along the path, $T_1$ is the tension force applied to the web sensed of upstream of the first position, and $T_2$ is the tension force applied to the web sensed downstream of the first position, and wherein the control system generates the speed control signal as a function of the determined first strain and determined second strain.

10. The system of claim 8, wherein the control system calculates a target speed for the web material at the first position along the path, calculates the first strain of the web material upstream of the first position along the pat, and wherein the control system is further responsive to the calculated target speed, the calculated first strain, and the sensed speed of the web material at the second position along the path, for providing the speed control signal.

11. The system of claim 10, wherein the control system provides the speed control signal by employing an algorithm that executes the equation:

$$V_T=V_2/(\in_T-\in_1+1);$$

where $V_T$ is the calculated target speed, $V_2$ is the speed of the web material sensed at the second position along the path, $\in_T$ is the target strain as indicated by the input device, and $\in_1$ is the calculated first strain.

12. The system of claim 10, wherein the control system provides the speed control signal to the feed device to increase the second tension force applied to the web material when the calculated second strain of the web material is less than the target strain range, and to decrease the second tension force applied to the web material when the calculated strain of the web material is greater than the target strain range.

13. The system of claim 12, wherein the input device generates a reference signal representative of the target strain input by an operator via the input device, and wherein the control system is responsive to the reference signal and the calculated strain for providing the speed control signal to the feed device to maintain the strain of the web material within the target strain range as indicated by the input device.

14. The system of claim 1, wherein the feed roller is mechanically linked to a motor for rotating the feed roller, wherein the motor is responsive to the speed control signal for adjusting the rotational speed of the feed roller and the tension force applied to the web material.

15. The system of claim 1, wherein the control system is a programmable logic controller (PLC) linked to and receiving inputs from the first speed sensor, the second speed sensor, the first tension sensor and the second tension sensor, wherein the PLC generates an output signal as a function of the received inputs, and wherein the feed roller is linked to the PLC for receiving an output.

16. The system of claim 1, wherein the input device is a user station linked with an absorbent garment manufacturing machine receiving the web material and producing absorbent garments therefrom.

17. The system of claim 16 wherein the user station stores the target strain range, and wherein the control system provides the speed control signal to the feed device as a function of the target strain range as stored on the user station, the first tension force sensed by the first force sensor, the second tension force sensed by the second tension sensor, the first speed sensed by the first speed sensor and the second speed sensed by second speed sensor.

18. A method for controlling a tension force applied to a web material traveling along a path comprising:

defining a target strain range for the web material;

calculating a strain of the web material;

adjusting the tension force applied to the web material as a function of the calculated strain, wherein the adjusting comprises increasing the tension force applied to the web material when the calculated strain of the web material is less than the target strain range, and wherein the adjusting comprises decreasing the tension force applied to the web material when the calculated strain of the web material is greater than the target strain range;

sensing a first speed of the web material at a first position along the path, sensing a second speed of the web material at a second position along the path, sensing a first tension of the web material upstream of the first position along the path, and sensing a second tension of the web material downstream of the first position along the path, and wherein the calculating comprises calculating the strain as a function of the sensed first speed, the sensed second speed, sensed first tension and sensed second tension.

19. The method of claim 18, wherein the calculating the strain comprises calculating a first strain of the web material upstream of the first position along the path, and calculating a second strain of the web material downstream of the web along the path the force applied to the web material, and wherein the adjusting comprises adjusting the tension force applied to the web material as a function of the calculated first strain and the sensed second speed.

20. The method of claim 18 further comprising producing absorbent garments from the web material.

21. The method of claim 18, wherein the target strain range includes a specific strain, and wherein the adjusting comprises increasing the tension force applied to the web material when the calculated strain is less than the specific strain, and wherein the adjusting comprises decreasing the tension force applied to the web material.

* * * * *

UNITED STATES PATENT AND TRADEMARK OFFICE
CERTIFICATE OF CORRECTION

PATENT NO.     : 6,851,593 B2
DATED          : February 8, 2005
INVENTOR(S)    : Paul A. Weber et al.

It is certified that error appears in the above-identified patent and that said Letters Patent is hereby corrected as shown below:

Column 17,
Line 65, "$\Delta L = (V_1 3] V_2) / t$" should read -- $\Delta L = (V_1 - V_2)/t$ --.

Column 24,
Line 20, "teed" should read -- feed --.
Line 40, "$\in_1 = [(V_2 - V_1)/V_1] \cdot [T_2/(T_2 - T_1)]$" should read -- $\in_1 = [(V_2 - V_1)/V_1] \cdot [T_1/(T_2 - T_1)]$ --.

Signed and Sealed this

Fifth Day of July, 2005

JON W. DUDAS
*Director of the United States Patent and Trademark Office*